(12) United States Patent
Panine et al.

(10) Patent No.: US 9,121,812 B2
(45) Date of Patent: Sep. 1, 2015

(54) COMPACT X-RAY ANALYSIS SYSTEM (75) Inventors: Pierre Panine, La Terrasse (FR); Peter Hoghoj, Saint Martin le Vinoux (FR)

(73) Assignee: XENOCS, Sassenage (FR)

( * ) Notice: Subject to any disclaimer, the term of this patent is extended or adjusted under 35 U.S.C. 154(b) by 340 days.

(21) Appl. No.: 13/522,622

(22) PCT Filed: Jan. 18, 2011

(86) PCT No.: PCT/EP2011/050568
§ 371 (c)(1),
(2), (4) Date: Jul. 17, 2012

(87) PCT Pub. No.: WO2011/086191
PCT Pub. Date: Jul. 21, 2011

(65) Prior Publication Data
US 2012/0294426 A1  Nov. 22, 2012

(30) Foreign Application Priority Data
Jan. 18, 2010 (FR) ........................ 10 50301

(51) Int. Cl.
G01N 23/00 (2006.01)
G01N 23/201 (2006.01)

(52) U.S. Cl.
CPC ................... *G01N 23/201* (2013.01)

(58) Field of Classification Search
CPC ..... G01N 23/20; G01N 23/201; G21K 1/025; G21K 1/06
USPC ................................ 378/70, 82, 84
See application file for complete search history.

(56) References Cited

U.S. PATENT DOCUMENTS 6,504,900 B2 *  1/2003 Kondo et al. ............ 378/70
6,807,251 B2 * 10/2004 Okanda et al. ........... 378/71

(Continued)

OTHER PUBLICATIONS

Diat et al., "Ultra-small-angle X-ray scattering with a Bonse-Hart camera on the high brilliance beamline at the ESRF", Nuclear Instruments and Methods in Physics Reasech A, vol. 356 (1995) pp. 566-572.

(Continued)

*Primary Examiner* — Michael Maskell
(74) *Attorney, Agent, or Firm* — Birch, Stewart, Kolasch & Birch, LLP (57) ABSTRACT

The invention relates to a device for the delivery of a beam of X-rays for analysis of a sample (50), comprising:
  a source block (100) comprising X-ray emission means;
  an optical block (200) placed downstream of the source block (100), said optical block (200) comprising an optical monochromator component (210) having a reflecting surface (212) provided for conditioning X-rays emitted by the source block (100) according to unidimensional or bidimensional optical effect; and
  definition means (300) of X-rays comprising:
    an anti-diffusing member (310) for spatially delimiting X-rays conditioned by the optical monochromator component (210), placed downstream of the optical monochromator component (210) and comprising one or more plates (311) having portions (313) arranged to form a delimiting orifice (312), said portions (313) being coated with a monocrystalline material limiting the scattering of X-rays;
    a cut-off member (320) of X-rays emitted by the source block (100), comprising X-ray absorption means arranged in the delivery device to cut off the direct X-ray beams likely to reach the spatial delimitation anti-diffusing member (310) without conditioning by the optical monochromator component (210).

19 Claims, 3 Drawing Sheets

(56) References Cited

U.S. PATENT DOCUMENTS

| | | |
|---|---|---|
| 6,990,177 B2 * | 1/2006 | Fujinawa et al. ............ 378/149 |
| 7,542,548 B2 * | 6/2009 | Matsuo et al. ................ 378/84 |
| 2008/0175352 A1 * | 7/2008 | Kogan ........................... 378/81 |

OTHER PUBLICATIONS

French Preliminary Search Report issued in French patent application No. 1050301 on Jul. 30, 2010.

Li et al., "Scatterless hybrid metal-single-crystal slit for small-angle X-ray scattering and high-resolution X-ray diffraction", Jounral of Applied Crystallography, vol. 41 (2008) pp. 1134-1139.

PCT Search Report issued in International application No. PCT/EP2011/050568 on Feb. 24, 2011.

Tang et al., "X-ray beam characteristics on MPW6.2 at the SRS", Nuclear Instruments and Methods in Physics Research B, vol. 222 (2004) pp. 659-666.

\* cited by examiner

COMPACT X-RAY ANALYSIS SYSTEM

FIELD OF THE INVENTION

The present invention relates to the field of analysis of samples by X-rays (RX), in particular analysis of samples by studying the scattering of X-rays (RX scattering) small-angle.

PRIOR ART

X-ray analysis, in particular analysis by study of the scattering of small-angle X-rays (called SAXS analysis, corresponding to the English acronym <<Small Angle X-ray Scattering>>), requires illuminating of the sample to be analysed with a beam of X-rays having increased quality, especially in terms of spatial and angular distribution of intensity of the beam. In fact, an SAXS analysis system requires an intense beam perfectly defined on the sample and on the detector with low divergence, as well as a beam size well defined in space so as to obtain a uniform profile of intensity in the plane of the sample and of the detector.

The detection limit of an SAXS system is defined by the minimum value of the wave vector $q_{min}$ associated with the sample which can be obtained by means of the relevant analysis system, the wave vector being inversely proportional to the structural parameter of the sample in real space. In the small-angle approximation of Bragg's law, applicable to SAXS applications, the wave vector is proportional to the angle of scattering. The detection limit $q_{min}$ is therefore associated with the minimum angle of scattering which can be detected, the detection of this angle being restricted by the size of beam on the sample, this beam then being transmitted to the detector. Because it is also necessary to block the beam transmitted by the sample before it reaches the detector so that this transmitted beam does not perturb the measuring of the scattered beam, it is necessary to increase the sample-detector distance to be able to effectively detect the beams diffused at small angles.

Figure 1:
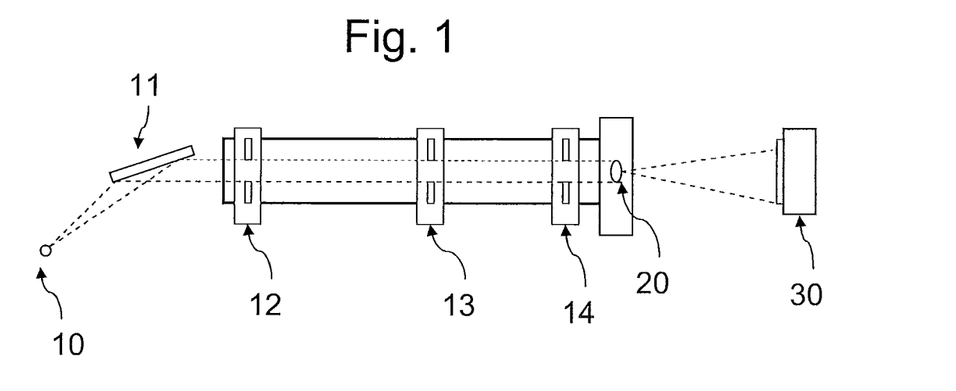

FIG. 1 illustrates an SAXS analysis system according to the prior art, comprising a monochromator mirror 11 coupled to a source of X-rays 10 and a collimation unit of the beam composed of three collimation members (12;13;14), the aim of this collimation unit being to spatially delimit the size of the beam of X-rays intended for the sample 20, at the same time preventing parasite scattering from interfering with the small-angle scattering signal produced by the sample and observed on the detector 30. In this system, the collimation members are composed of a plate formed from an absorbent metallic material comprising an orifice in the form of a hole (<<pinhole>> in English) or a slit. The first collimation member 12 is provided for a first spatial delimitation of the beam of X-rays, the second collimation member 13 as such cuts off the parasite beam originating from the first collimation member 12, that is, the scattered beam on the edges of the collimation member 12, and the last collimation member 14 defines the size of beam on the sample, which has a direct impact on the signal intensity which will be diffused by the sample (definition of the quantity of sample illuminated), but also on the detection limit of the system.

One of the disadvantages of this type of system comes from the fact that, to reduce the parasite signal diffused at the level of the collimation members (slits and pinholes), the flow is substantially reduced (reduction of the opening of the second slit especially), resulting in longer analysis and signal intensity diffused by the sample, which are lower (loss of the order by a factor of 3). Also, such systems are particularly bulky, since the length of the definition unit is generally well over a meter.

Figure 2:
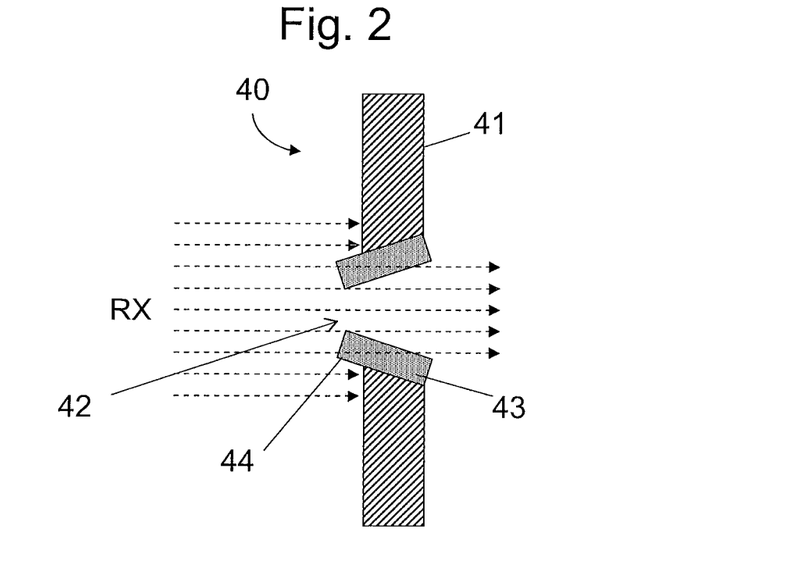

A novel type of hybrid slits has recently been proposed, which in part resolves the disadvantages cited above when they are used in X-ray analysis systems. Such a type of slit 40 is illustrated in FIG. 2 (sectional view) and is described in detail in the publication entitled <<Scatterless hybrid metal-single-crystal slit for small-angle X-ray scattering and high-resolution X-ray diffraction>> by Youli Li et al. (J. Appl. Cryst. (2008). 41, 1134-1139). The principle of these anti-diffusing hybrid slits consists of using a plate 41 of material absorbing X-rays (e.g. material based on metal of tungsten or brass type) wherein a slit 42 is made, and covering the lips of the slit 42 in monocrystalline material 43 so as to limit any scattering on the ridges or the edge of the slit 42. The crystalline plane is oriented relative to the incident beam so as to limit any Bragg diffraction which might cause parasite scattering. Also, to limit any grazing incidence diffraction, the edge of the slits 42 is inclined relative to the RX beam as per an angle of a few degrees to a few tens of degrees. Also, as is illustrated in FIG. 2, the crystal 43 is positioned on the lips of the slit 42 so as to project relative to the plate, creating a protuberance 44 along the width of the slit 42, to avoid any ridge of the slit 42 being touched by the incident RX beam which could cause parasite scattering.

The outcome of this geometry consisting of inclining the crystal relative to the incident beam is that the absorption profile of these slits is progressive and depends on the inclination of the monocrystalline part as well as on the atomic number of the element making up the crystal. In fact, a certain part of the beam passing through the crystalline material only is more or less absorbed along the zone through which it traverses the crystal due to variation in thickness of the crystalline material effectively passed through (the beam is absorbed very weakly when it passes through near the protuberance and a little more so when it passes through near metallic ridge of the absorbent material).

It has consequently been proposed to utilise such hybrid slits for improving existing X-ray analysis systems of small-angle scattering, especially for forming the collimation unit to be placed between the delivery device of the beam of X-rays and the sample. Youli Li et al. propose in particular replacing the three-slit configuration explained hereinabove by a configuration comprising two successive anti-diffusing hybrid slits the function of which is to delimit the size of the beam while avoiding any parasite scattering.

The use of such hybrid slits simplifies the configuration of the collimation unit of the analysis system, and also substantially increases the flow of X-rays to the sample. A major disadvantage however is the regret that this relates to the bulk of the system since the necessary distances between the different elements of the system are unchanged, with a distance between the outlet of the X-ray delivery device and the sample (distance imposed by the necessary spacing for the collimation unit) always over a meter (of the order of 1.50 m).

An aim of the present invention is therefore to propose an X-ray delivery device for analysis of a sample by X-ray, which resolves at least one of the above disadvantages.

In particular, an aim of the present invention is to propose an X-ray delivery device which is compact and adapted to be used in a compact analysis system of a sample by X-ray, at the same time providing a beam of X-rays to the sample which has increased quality, especially in terms of spatial and angular distribution of intensity of the beam.

Another aim of the present invention is to propose a delivery device of X-rays and an analysis system of an associated sample by X-ray particularly adapted for the study of samples by scattering of small-angle X-rays.

EXPLANATION OF THE INVENTION

A delivery device of a beam of X-rays for analysis of a sample is proposed for this purpose, the sample being placed at the output of said delivery device, characterised in that the delivery device comprises:

a source block comprising X-ray emission means;

an optical block placed downstream of the source block relative to the direction of propagation of the X-rays, said optical block comprising an optical monochromator component having a reflecting surface provided for conditioning X-rays emitted by the source block according to a unidimensional or bidimensional optical effect; and definition means of X-rays comprising:

a spatial delimitation X-ray anti-diffusing member conditioned by the optical monochromator component, said delimitation member being set downstream of the optical monochromator component relative to the direction of propagation of the X-rays, said spatial delimitation anti-diffusing member comprising one or more plates having portions arranged to form a delimiting orifice, said portions being coated with a monocrystalline material limiting the scattering of X-rays;

a cut-off member of X-rays emitted by the source block, said cut-off member comprising X-ray absorption means arranged in the delivery device to cut off the direct X-ray beams emitted by the source block likely to reach the spatial delimitation anti-diffusing member without conditioning by the optical monochromator component.

The fact of using a cut-off member for cutting off direct X-ray beams likely to reach the spatial delimitation anti-diffusing member without conditioning by the optical monochromator component, in combination with the other elements of the system, allows a particularly compact delivery device, since the spatial delimitation anti-diffusing member can be brought considerably closer to the optical monochromator component while having improved quality for the beam of X-rays on the sample.

Preferred but non-limiting aspects of this device, taken together or in combination, are the following:

the X-ray absorption means of the cut-off member are arranged to prevent direct X-ray beams from going beyond the optical monochromator component in the direction of propagation of the X-rays.

the cut-off member comprises an absorption plate formed from material absorbing X-rays and including a definition orifice, said absorption plate being arranged upstream of the optical monochromator component relative to the direction of propagation of the X-rays, and said definition orifice having dimensions and positioning provided to cut off the direct X-ray beams emitted by the source block likely to reach the delimiting collimating member without conditioning by the optical monochromator component.

which definition orifice of the cut-off member has reduced dimensions and positioning provided to cut off some of the optical X-ray beams emitted by the source block directly impacting the reflecting surface of the optical monochromator component.

the definition orifice of the cut-off member comprises inclined edges coated by monocrystalline material provided to prevent the scattering of X-rays on said edges.

the definition orifice and the delimiting orifice have the form of a slit or a hole, the hole being preferably rectangular, square or circular.

the absorption plate, the optical monochromator component and the spatial delimitation anti-diffusing member are fixed on the same monolithic support.

the absorption plate, the optical monochromator component and the spatial delimitation anti-diffusing member are arranged inside a casing adapted to be put under vacuum, said casing comprising inlet and outlet walls formed from material transparent to X-rays.

the cut-off member comprises an absorption blade formed from material absorbing X-rays, said absorption blade being placed in the optical block opposite the optical monochromator component so as to cut off the X-rays likely to reach the delimiting collimating member without conditioning by the optical monochromator component.

the absorption blade comprises an inclined edge and coated in a monocrystalline material provided to prevent the scattering of X-rays on said edge.

the optical monochromator component is curved according to a sagittal direction following a meridional direction relative to the direction of propagation of the X-rays, the absorption blade being arranged at the centre of the optical monochromator component so as to brush the reflecting surface.

the absorption blade has a form complementary to the optical monochromator component.

which spatial delimitation anti-diffusing member comprises a plate in which is formed the delimiting orifice, said delimiting orifice comprising inclined edges coated with the monocrystalline material provided to prevent the scattering of X-rays on said edges.

which spatial delimitation anti-diffusing member comprises several plates, each plate having an inclined edge coated with the monocrystalline material provided to prevent scattering of X-rays on said edge, said plates being arranged relative to each other such that said edges form the delimiting orifice in the direction of propagation of the X-rays.

the distance between the outlet of the optical monochromator component and the inlet of the spatial delimitation anti-diffusing member is 15 cm.

the delivery device also comprises a complementary cut-off member placed between the optical monochromator component and the spatial delimitation anti-diffusing member, said complementary cut-off member comprising an X-ray absorption plate in which is formed a complementary definition orifice, the complementary definition orifice having dimensions and positioning provided to cut off some of the X-rays conditioned by the optical monochromator component.

the reflecting surface of the optical monochromator component is formed by a multilayer coating, said optical monochromator component being also suitable for collimation of X-rays impacting said optical monochromator component in the direction of the sample.

Also, an X-ray analysis system of a sample is proposed, which comprises such an X-ray delivery device intended to be placed upstream of the sample to be analysed, the system also comprising an X-ray detector placed downstream of the sample, and intended especially to collect X-rays emitted by the sample.

In this case, the reflecting surface of the optical monochromator component can be formed by a multilayer coating, said optical monochromator component also being suitable for focussing on the detector X-rays impacting said optical monochromator component.

DESCRIPTION OF THE FIGURES

Other characteristics and advantages of the invention will emerge from the following description which is purely illustrative and non-limiting and must be considered in conjunction with the attached diagrams, wherein, apart from FIGS. 1 and 2 illustrating the prior art.

DETAILED DESCRIPTION OF THE INVENTION

An X-ray delivery device generally comprises a source block 100 adapted to send X-rays, this source block 100 being coupled to an optical block 200 for conditioning these X-rays emitted by the source block 100 in the direction of the sample 50 to be analysed.

The source block 100 therefore comprises a source S of X-rays adapted to generate a beam of X-rays, for example comprising lines of monochromatic emissions such as lines of fluorescence of a target material comprising part of the source. The source S can be typically a source for electrons-material interaction of sealed tube type or of rotating anode type for which interaction at the origin of the emission of X-rays is electrons-material interaction, or a laser source for which the generation of X-rays occurs via laser-material interaction.

Situated downstream of the source block 100 relative to the direction of propagation $P_{RX}$ of the X-rays, the optical block 200 preferably comprises an optical monochromator component 210 for filtering parasite lines and braking radiation (radiation commonly called <<Bremsstrahlung>>) emitted by the source S with the aim of obtaining a beam the spectral resolution of which is adapted to perform SAXS analysis especially. Preferably, the optical monochromator component 210 comprises a support 211 having a specific conformation, this support 211 being covered with a reflecting surface 212 provided to condition the X-rays emitted by the source block 100 according to a unidimensional or bidimensional optical effect (that is, conditioning according to one or two directions of space). Even more preferably, the optical monochromator component 210 is suitable for ensuring focussing or collimation of the divergent beam emitted by the source S so as to form the beam of X-rays in the direction of the sample 50 and of the detector 60 of X-rays placed downstream of the X-ray delivery device.

Figure 3:
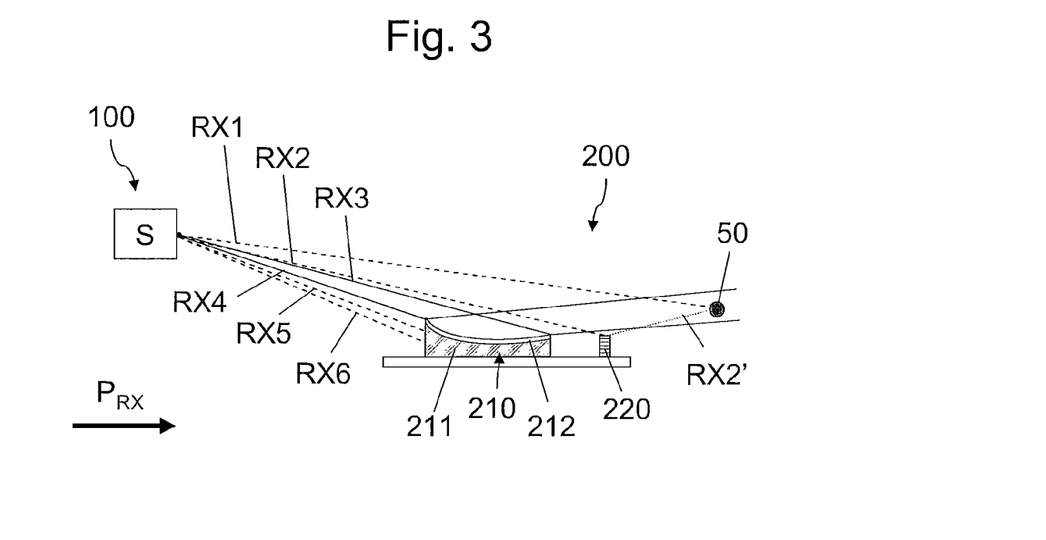
FIG. 3 is a diagram illustrating the propagation of X-rays emitted by a source block in the direction of an optical block comprising an optical monochromator component.

FIG. 3 illustrates the propagation of the X-rays emitted by the source block 100 in the direction of the optical block 200 then of a sample 50 which would be positioned near the optical block, that is, typically less than 15 centimeters relative to outlet of the optical monochromator component. Of the different direct X-ray beams (RX1, RX2, RX3, RX4, RX5, RX6) emitted by the source S, these can be classified into several categories according to their progression in the optical block 200. Direct beam of X-rays means any beam of X-rays emitted by the source S without undergoing diffraction.

First there are (RX3, RX4) beams known as <<optical beams>>, which correspond to the direct beams directly impacting (that is, without diffraction or prior scattering) the optical monochromator component 210. These optical beams are suitable by the optical monochromator component 210 in the direction of the sample 50, and can be used (at least in part) for analysis of said sample 50. Of these optical beams, the beams necessary for analysis of the sample are qualified as <<useful beams>>. These useful beams can correspond to all the optical beams conditioned by the optical monochromator component, or can constitute part only of these optical beams. In this last case, means for cutting off some of the non-useful optical beams can be used. In particular, the useful beams can be defined by a member comprising a delimiting orifice placed at the inlet and/or at the output of the optical monochromator component. This delimitation of the optical beam to a useful beam can be done according to the sagittal direction (direction perpendicular to the plane of FIGS. 3 to 6), and/or along the length of the optical monochromator component, that is, in the meridional direction corresponding to the general direction of propagation of the X-rays.

All the other direct beams of (RX1, RX2, RX5, RX6) X-rays emitted by the source S are not reflected by the optical monochromator component, and therefore cannot be <<useful>> for analysis.

Of the X-ray beams (RX1, RX2, RX5, RX6) which are not going to impact the optical monochromator component 210, the direct X-ray beams (RX1, RX2) emitted by the source block likely to reach the sample 50 without conditioning by the optical monochromator component 210 can be categorised. Some X-ray beams RX1 can actually directly reach this sample 50 without undergoing diffraction in the optical block 200, whereas other RX2 X-ray beams can reach the sample 50 indirectly, that is, by undergoing diffraction in the optical block 200. This will be the case for example of diffused RX2' beams originating from the impacting of the direct beam of RX2 X-rays on an opto-mechanical 220 member set in the optical block 200.

Other direct X-ray beams (RX5, RX6) are emitted in a direction such that in any case they will be stopped by the optical monochromator component 210, and more precisely by the support 211. Preferably, the support 211 of the optical monochromator component 210 is formed from material absorbing X-rays and preventing any scattering.

All X-ray beams striking the sample 50 without having been conditioned by the optical monochromator component 210 now perturb X-ray analysis done of the sample 50, these beams being called parasite beams.

As a consequence, it is preferable for the analysis system by X-rays to be provided to limit the influence of such beams, while offering a beam of X-rays delivered to the sample with substantial quality and intensity. For this purpose, it is proposed in particular to cut off the direct beams of type RX1 and RX2, that is, the direct beams located in the source/optical component sight line (the sight line being defined by the axis [source—optical component inlet] (corresponding to RX4) and the axis [source—optical component outlet] (corresponding to RX3) with a deviation of a few degrees around these axes).

To achieve this, it is proposed to use a X-ray delivery device which, other than the source block 100 and the optical block 200 presented earlier, comprises means for defining X-rays 300, these definition means 300 comprising in combination:

an anti-diffusing member 310 for spatially delimiting X-rays conditioned by the optical monochromator component 210, said delimitation member 310 being set downstream of the optical monochromator component 210 relative to the direction of propagation $P_{RX}$ of X-rays; and a cut-off member 320 of X-rays emitted by the source block 100, said cut-off member 320 comprising X-ray absorption means 321 arranged in the delivery device to cut off the direct X-ray beams emitted by the source block 100 likely to reach the spatial delimitation anti-diffusing member 310 without conditioning by the optical monochromator component 210.

The cut-off member 320 therefore prevents X-ray beams from having been reflected by the optical monochromator component 210 being able to reach the sample 50 placed downstream of the spatial delimitation anti-diffusing member 310.

One solution used conventionally to reduce the influence of parasite beams is to place the delimitation element sufficiently far from the optical monochromator component 210, such that these parasite beams cannot reach and pass through the delimitation window.

In the present invention, the use of the cut-off member 320 is therefore particularly advantageous since this brings the element closer, realising the spatial delimitation of the beam of X-rays, forming a highly compact system.

Better still, the spatial delimitation anti-diffusing member 310 can even be arranged to be integrated in the X-ray delivery device (for example in or at the output of the optical block 200), greatly simplifying the RX analysis system which therefore does not need to have a specific delimitation unit provided as a complement to the X-ray delivery device.

These spatial delimitation X-ray anti-diffusing members 310 and cut-off members 320 are presented in detail hereinbelow.

The spatial delimitation anti-diffusing member 310 is intended to produce a uniform and refined beam profile, directly at the X-ray beam delivery device output.

The main property of X-rays comes from their wavelength, their interaction with the material operating on the scale of this length, that is, of the order of an Angstrom (Å). In this way, any physical presence positioned in a beam of X-rays having a size exceeding a few Angstroms has a non-negligible effect on the quality of the RX beam, generating a scattering signal, diffraction signal, etc. In this sense, any object used for spatially delimiting the intensity distribution does affect the quality of the beam of X-rays illuminating the sample, this contribution being called parasite contribution or parasite signal.

It is therefore proposed here to use a spatial delimitation member specially adapted to reduce, or even cancel out, the parasite signal (originating for example from the scattering at the edges of the delimitation window of the member). To do this, the spatial delimitation anti-diffusing member 310 comprises one or more plates 311 having portions 313 arranged to form a delimiting orifice 312, said portions 313 being coated with monocrystalline material limiting the scattering of X-rays.

This provides a single spatial delimitation member in the analysis system, and therefore simplifies this system and reduces its bulk. Also, coupled to the cut-off member 320, this spatial delimitation anti-diffusing member 310 can be placed near (for example at a distance of under 15 cm) the outlet of the optical monochromator component (the outlet corresponding to the end of the optical monochromator component located downstream relative to the direction of propagation of X-rays), further boosting the compactness of the system.

The spatial delimitation anti-diffusing member 310 is preferably formed according to a structure such as proposed by Youli Li et al. in his publication called <<Scatterless hybrid metal-single-crystal slit for small-angle X-ray scattering and high-resolution X-ray diffraction>> (J. Appl. Cryst. (2008). 41, 1134-1139).

In particular, the plates 311 are formed from material absorbing X-rays, for example metal-based material such as tungsten, lead, or brass. These plates can have a thickness of a few millimeters, of the order of 2 mm for example. The monocrystalline material used to limit the scattering of X-rays is as such preferably silicon, especially in the case of an RX source emitting copper Kα radiation, or germanium, especially in the case of an RX source emitting molybdenum Kα radiation.

The configuration of the spatial delimitation anti-diffusing member 310 can also be more or less complex.

The simplest configuration consists for example of a single plate 311 wherein the delimiting orifice 312 is formed, said delimiting orifice 312 comprising inclined edges 313 coated with the monocrystalline material provided to prevent the scattering of X-rays on said edges 313. The delimiting orifice 312 can for example be a slit (for unidimensional analysis), or a hole (for bidimensional analysis) having a circular, square or rectangular form.

According to a more complex configuration (not illustrated), the spatial delimitation anti-diffusing member 310 comprises several plates 311, each plate having an inclined edge 313 coated with monocrystalline material provided to prevent the scattering of X-rays on said edge, said plates 311 being arranged relative to each other such that said edges form the delimiting orifice in the direction of propagation of the X-rays.

The spatial delimitation anti-diffusing member 310 can for example comprise two plates 311 whereof the edges 313 are arranged opposite such that the spacing between the plates 311 forms a spatial delimitation slit 312. In this case, the corresponding RX analysis is analysis of unidimensional type, that is, the profile of the scattered beam is analysed according to a dimension in the case of an SAXS system. The collimating member is coupled to an optical monochromator component producing a unidimensional optical effect such as focussing or collimation in a plane of space.

When the delimiting orifice 312 is to have the form of a hole rather than a slit according to this complex configuration, the spatial delimitation anti-diffusing member 310 then comprises two sets of two plates 311, the two plates 311 of each set being arranged opposite relative to each other to form a delimitation slit. These two sets of plates are positioned one after the other in the direction of propagation of the X-rays, the plates being parallel to each other. These sets are also arranged such that the delimitation slit of the second set of plates is transversal to the delimitation slit of the first set of plates, forming a delimiting orifice in the form of a rectangular hole oriented in the direction of propagation of the X-rays. In this case, the corresponding RX analysis is analysis of bidimensional type. The collimating member is coupled to an optical monochromator component producing a bidimensional optical effect such as collimation in two planes of space or focussing on a single point. An arrangement comprising more than four blades forming a pseudo-circular orifice could also be provided similarly to a photographic iris.

An advantage associated with the complex configuration of the spatial delimitation anti-diffusing member 310 is being able to vary the size of the delimiting orifice 312 simply by changing the relative positioning of the plates 311. Also, these plates 311 can be mounted on a motorised sliding mechanism for easier handling.

The spatial delimitation X-ray anti-diffusing member 310 generally comprises the outlet of the delivery device proposed. The sample 50 is positioned immediately at the outlet of this delivery device, that is, immediately after the spatial delimitation anti-diffusing member 310 at the level of the delimiting orifice 312. The analysis system which comprises such an X-ray delivery device as well as a detector placed downstream of the sample is therefore particularly compact relative to existing devices.

As pointed out earlier, the cut-off member 320 comprises X-ray absorption means 321 arranged in the delivery device to cut off the direct X-ray beams emitted by the source block 100 likely to reach the spatial delimitation anti-diffusing member 310 without conditioning by the optical monochromator component 210. It prevents X-ray beams which would not or are not reflected by the optical monochromator component 210 from being able to reach the sample 50 placed downstream of the spatial delimitation anti-diffusing member 310. The absorption means are preferably formed from material adapted to absorb X-rays of energies reaching at least 60 keV.

Preferably, the X-ray absorption means 321 of the cut-off member 320 are arranged in the optical block 200 to prevent the parasite X-ray beams from going beyond the optical monochromator component 210 in the direction of propagation of the X-rays. Because of this, the cut-off member 320 cuts off any direct beam which is not going to reflect on the optical monochromator component 210, and which would be likely to reach the sample 50. This also avoids such direct beams from impacting another component of the optical block 200 and therefore scattering, in particular in the direction of the sample 50.

Figure 4:
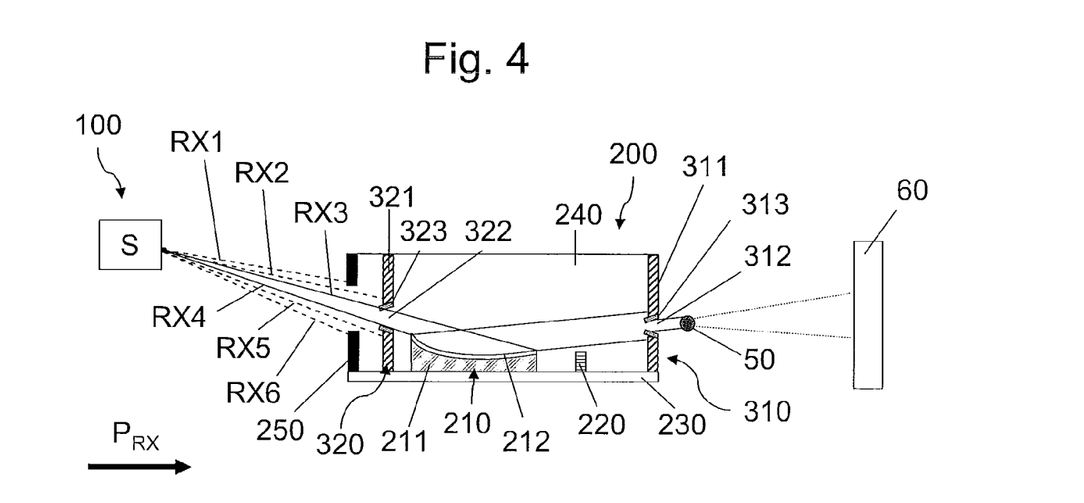
FIG. 4 is a diagram illustrating a delivery system of X-rays integrated in an analysis system of a sample, according to a first embodiment of the invention.

According to a first embodiment such as illustrated in FIG. 4, the cut-off member 320 comprises an absorption plate 321 formed from material absorbing X-rays, such as for example metal-based material (e.g. tungsten, lead, brass). Arranged in this absorption plate 321 also is a definition orifice 322 for example in the form of a slit or hole (e.g. circular or rectangular).

This absorption plate 321 is preferably arranged upstream of the optical monochromator component 210 relative to the direction of propagation of the X-rays. It can for example be plated to the inlet of the optical monochromator component 210.

The definition orifice 322 of this absorption plate 321 has dimensions and positioning provided to cut off the direct X-ray beams emitted by the source block 200 which are likely to reach the spatial delimitation anti-diffusing member 320 without conditioning by the optical monochromator component 210. More precisely, the aim of this absorption plate 321 is to prevent the direct beams likely to impact the delimitation member 310 from entering the optical block 200, considerably reducing the presence of parasite beams at the level of the sample 50.

In the embodiment illustrated in FIG. 4, the absorption plate 321 and the corresponding definition orifice 322 are arranged so as to cut off both the direct beams (RX2) likely to impact the spatial delimitation member 320 without conditioning by the optical monochromator component 210, as well as other direct beams (RX5) which in any case would be absorbed by the support 211 of the optical monochromator component 210. The absorption plate 321 and the corresponding definition orifice 322 could however be arranged so as to cut off only those direct beams (RX2) likely to impact the spatial delimitation member 320 without conditioning by the optical monochromator component 210. The absorption plate 321 especially cuts off direct beams situated in the sight line of the optical monochromator component 210 which are not cut by the mechanical elements of the delivery system of X-ray beams set upstream of the optical monochromator component 210, such as for example the inlet flange 250 of the optical block 200. In the absence of such an inlet flange 250, for example when the absorption plate 321 comprises the inlet of the optical block 200, this absorption plate 321 also absorbs the direct beams RX1 and RX6.

By way of indication it is specified that the absorption means used to cut off the direct beams situated in the sight line of the optical monochromator component will be dimensioned so as to cut off a majority of the direct beam, given that a residual flow, though of low quantity, could subsist in the sight line of the optical monochromator component because of manufacturing precisions of these elements. This residual flow will be typically less than 1% of the beam reflected by the optical monochromator component within the scope of the invention.

According to a more preferred configuration, the definition orifice 322 of the absorption plate 321 has reduced dimensions and positioning provided to cut off part of the optical X-ray beams emitted by the source block 100 and which would have to directly impact the reflecting surface 212 of the optical monochromator component 210. Such a configuration ensures that all direct parasite beams likely to impact the delimitation member are cut off before entering the optical block 200.

According to an even more preferred configuration, the cut-off member also assumes the role of definition of the useful beam for RX analysis of the sample. In this embodiment the definition member comprises absorption means 326 arranged in the delivery device so as to limit at the output of the optical monochromator component 210 the beam conditioned by the latter to the useful beam threshold for RX analysis by simultaneously cutting off the direct X-ray beams emitted by the source block likely to reach the spatial delimitation anti-diffusing member without conditioning by the optical monochromator component, and some of the optical non-useful beams for RX analysis.

In particular, in the case where the optical monochromator component is a component which comprises a suitable diffractive surface for producing a focussing or collimation effect, the useful surface is typically less than the real surface especially in the sagittal direction which is the direction perpendicular to the plane of FIG. 4.

Figure 7:
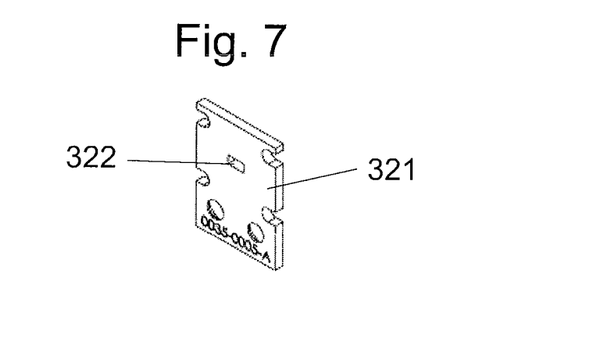
FIG. 7 illustrates a particular embodiment of a cut-off member which can be used in the analysis system of FIG. 4 or FIG. 6.

According to the embodiment consisting of applying the cut-off member upstream and/or downstream of the optical monochromator component, the definition means 320 respectively block the portion of the beam of X-rays impacting non-useful zones of the optical monochromator component and/or block the X-ray beams conditioned by the non-useful zones of the optical monochromator component to ensure definition of the useful beam for RX analysis. FIG. 7 illustrates the form which such an absorption plate 321 can take.

According to an embodiment of the invention, the definition orifice 322 of the absorption plate 321 comprises inclined edges 323 coated with monocrystalline material provided to prevent scattering of X-rays on said edges 323. In this case, the structure of this absorption plate 321 can be very similar to that of the spatial delimitation anti-diffusing member 310. It could even be envisaged that the cut-off member 320 comprises one or more sets of two plates arranged to form the preferred definition orifice 322 in the same way as for the spatial delimitation anti-diffusing member 310.

To efficaciously implement this variant of the cut-off member 320 where the edges of the absorption plate 321 are coated with an anti-diffusing edge, positioning of the absorption plates 321 at the output of the optical monochromator component is preferred.

More preferably, the absorption plate or the absorption plates 321, the optical monochromator component 210 and the spatial delimitation anti-diffusing member 310 are fixed on the same monolithic support 230. Such an embodiment enables precise alignment of the different elements relative to each other, optimising the cut-off function of the cut-off member 320 as well as the function of spatial delimitation 310 of the spatial delimitation anti-diffusing member 310. According to a particular embodiment the support 211 of the suitable component optical can constitute the monolithic support of the definition member 320 and of the spatial delimitation anti-diffusing member 310. In particular, the definition member 320 can be placed against the inlet of the optical monochromator component 210.

According to an even more preferred embodiment, the absorption plate 321, the optical monochromator component 210 and the spatial delimitation anti-diffusing member 310 form an integral part of the optical block 200 and are placed inside a casing 240 adapted to be placed under vacuum. This casing 240 preferably comprises inlet and outlet walls formed from material transparent to X-rays. It is understood that this transparent material is material which does not scatter X-rays. According to a variant, the inlet and outlet walls of this casing 240 are formed by the absorption plate 321 of the cut-off member 320 and by the spatial delimitation anti-diffusing member 310 respectively, these members in this case comprising means for placing the optical block 200 under vacuum. Membranes for placing under vacuum transparent to X-rays at the level of the definition orifices 322 and delimitation orifices 312 can be provided, for example. These membranes will be formed from material whereof the chemical composition and structure will be judiciously selected not to generate RX scattering.

Figure 5:
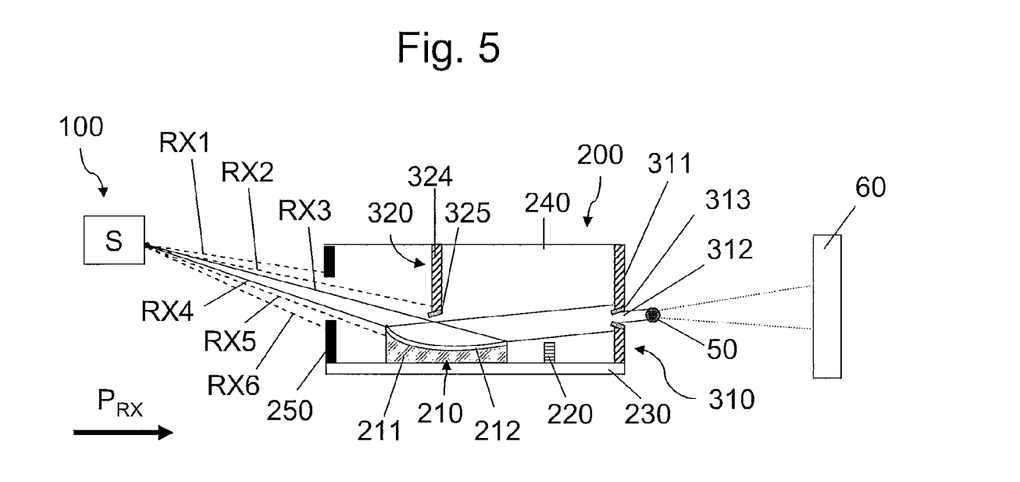
FIG. 5 is a diagram illustrating a delivery system of X-rays integrated in an analysis system of a sample, according to a second embodiment of the invention.

According to another embodiment of the invention, such as illustrated in FIG. 5, the cut-off member 320 comprises an absorption blade 324 formed from material absorbing X-rays, said absorption blade 324 being placed in the optical block 200 opposite the optical monochromator component 210 so as to cut off those X-rays likely to reach the spatial delimitation anti-diffusing member 310 without conditioning by the optical monochromator component 210.

The absorption blade 324 is formed from material absorbing X-rays, such as for example metal-based material (e.g. tungsten, lead, brass). In the case of unidimensional analysis, a single absorption blade 324 can be used, placed transversally relative to the direction of propagation of the X-rays. In the case of bidimensional analysis, it is preferable to use several absorption blades 324 arranged to cut off the X-ray beams according to several directions.

Preferably, the absorption blade or the absorption blades comprise an inclined edge 325 coated in a monocrystalline material (such as silicon for example) provided to prevent scattering of X-rays on said edge.

In general, the optical monochromator component 210 is curved in a sagittal direction and in a meridional direction relative to the direction of propagation of the X-rays. These meridional and sagittal directions are defined relative to the general direction of propagation of the beam of X-rays as follows:

The meridional direction corresponds to the average direction of propagation of this beam (and more precisely to the average direction between the average directions of propagation of the beam before and after its reflection on the optical conditioning unit of the beam, comprising for example an optical monochromator component), The sagittal direction corresponds to a transversal horizontal direction of this meridional direction (the vertical being defined here by the average normal to the part of the reflecting surface of the optical unit and which is effectively used to reflect the incident beam of X-rays). The sagittal direction corresponds to the direction perpendicular to the plane of FIGS. 3 to 6.

So, in the case where the optical monochromator component 210 is curved in a sagittal direction and in a meridional direction, the absorption blade 324 is preferably arranged at the centre of the optical monochromator component 210 so as to brush the reflecting surface 212. Such a configuration effectively absorbs the maximum of those X-rays not being reflected by the reflecting surface 212 of the optical monochromator component 210, without as such cutting off the useful beams of the latter.

More preferably still, the absorption blade or the absorption blades 324 have a form complementary to the optical monochromator component 210, so as to be the closest possible to the reflecting surface 312, and this irrespective of the form of the optical monochromator component 210.

It should be noted that in the case where the cut-off member 320 comprises only the absorption blade or the absorption blades 324, it is preferable that the optical block 200 comprises upstream of the optical monochromator component 210 a window 250 for delimiting X-rays which cuts off at least some of the X-ray beams emitted by the source S.

Also, in the same way as earlier, all the components of the optical block 200 can be integrated into a casing 240, according to a configuration similar to that presented above.

Figure 6:
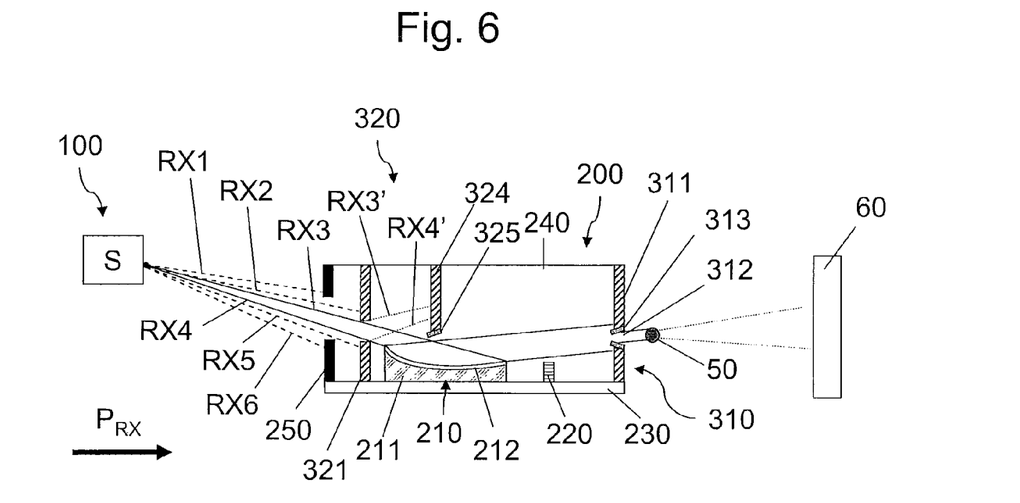
FIG. 6 is a diagram illustrating a delivery system of X-rays integrated in an analysis system of a sample, according to a third embodiment of the invention.

According to yet another embodiment of the invention such as illustrated in FIG. 6, the cut-off member 320 comprises at the same time the absorption plate or the absorption plates 321 presented hereinabove in reference in FIG. 4, and the absorption blade or the absorption blades 324 presented hereinabove in reference in FIG. 5.

Such a configuration increases analysis quality since the system has two complementary means preventing parasite beams from reaching the sample 50 to be analysed. According to this embodiment, the cut-off member 320 tends to cancel out all X-ray beams likely to reach the spatial delimitation anti-diffusing member 310. In the case where some of these beams would not have been cut, or where diffused (RX3', RX4') beams would have been emitted, in particular in the case where the absorption plate 321 has no edges provided to limit scattering (especially when this plate 321 has no inclined edges coated with monocrystalline material), then the absorption blade 324 placed in the optical block 200 reinforces and finalises the action of the absorption plate 321, ensuring the preferred function of cutting.

Also, in one or the other of the different embodiments presented hereinabove, the optical block 200 can also include a complementary cut-off member (not shown) placed between the optical monochromator component 210 and the spatial delimitation anti-diffusing member 310, said complementary cut-off member comprising an absorption plate in which is formed a complementary definition orifice, the complementary definition orifice having dimensions and positioning provided to cut off some of the X-rays conditioned by the optical monochromator component.

In the same way as the absorption plate 321 of the cut-off member principal 320, the complementary definition orifice transmits only some of the beams conditioned by the optical monochromator component 210 in the direction of the sample 50, and therefore forms a useful beam of X-rays reduced relative to the optical beam of X-rays.

The presented configuration of the X-ray delivery device implements a compact and effective analysis system, that is, with little parasite scattering. This uses in particular a particularly compact SAXS analysis system while retaining levels of resolutions adapted to the preferred applications.

According to a preferred application, the optical monochromator component has a multilayer reflecting surface, and is suitable for focussing the beam of X-rays emitted by the source on the detector. The definition and spatial delimitation of X-rays which can be done over short lengths (of maximum distance between the optical and the delimitation member of 15 cm), it is possible to utilise a mirror focussing on the detector with a dimension spot of less than 300 micrometers, at the same time retaining a sufficiently wide space between the sample and the detector, resulting in detection limits ($q_{min}$) adapted to a certain number of applications, such as for example SAXS analysis on protein solutions.

The crystallography of proteins determines the three-dimensional structure of proteins. The current tendency is characterisation of proteins of ever-increasing size and complexity. Such assemblies of proteins are difficult to crystallise. A characterisation tool available for the biologist and crystallographer researcher is RX analysis by small-angle scattering. In fact, if the structure of proteins in the form of crystals offers resolution of the order of an angstrom, scattering small-angle offers resolution rather of the order of 5 to 10 angstroms. The information obtained relates therefore to the envelope (the shape) of the protein. This information is of high value especially if the system being studied cannot crystallise. In the case where the system can crystallise, validation of the crystallographic model by the SAXS technique also has a high value by validating or invalidating the structural model, by placing the envelope measured by SAXS on the crystallographic measurement.

To determine the radius of gyration of the protein solution and its molecular weight a resolution limit of $q_{min}$ equal to $1^{e}$–$2$ Å$^{-1}$ will cover the majority of studied systems as well as a resolution $\Delta q$ (Å$^{-1}$) of $5^{e}$–$3$ Å$^{-1}$.

Possible configurations of the analysis system for such SAXS analysis are the following:

The compact configurations described hereinabove can therefore be realised by means of the proposed beam delivery device which is particularly compact. The optical configurations described hereinabove are also adapted to the realisation of a system for crystallography of proteins since the spot size produced by means of a source of 50 micrometers is of the order of 200 to 250 micrometers on the focal point.

It is therefore possible by means of the proposed X-ray beam delivery device to have an analysis system adapted to several analyses by means of a single system comprising a source and a single lens.

As is evident from the preceding description, the proposed analysis system is particularly advantageous for SAXS study analysis of the scattering of small-angle X-rays, but it has advantages allowing it to be used in any other type of analysis by X-rays, such as for example more conventional X-ray diffraction studies (called XRD analysis, corresponding to the English acronym <<X-Ray Diffraction>>), studies of the scattering of wide-angle X-rays (called WAXS analysis, corresponding to the English acronym <<Wide Angle X-ray Scattering>>), or studies by X-ray fluorescence (called XRF analysis, corresponding to the English acronym <<X-Ray Fluorescence>>).

The reader will have understood that numerous modifications can be made without departing materially from the novel ideas and advantages described here. Consequently, all modifications of this type are intended to be incorporated within the scope of the delivery device of beam of X-rays according to the invention.

The invention claimed is:

1. A device for delivery of a beam of X-rays for analysis of a sample, the sample being placed at the output of said delivery device, characterised in that the delivery device comprises:
a source block comprising X-rays emission means;
an optical block placed downstream of the source block relative to the direction of propagation of the X-rays ($P_{RX}$), said optical block comprising an optical monochromator component having a reflecting surface provided for conditioning X-rays emitted by the source block according to a unidimensional or bidimensional optical effect; and
definition means of X-rays comprising:
an anti-diffusing member for spatially delimiting X-rays conditioned by the optical monochromator component, said spatial delimitation anti-diffusing member being arranged downstream of the optical monochro-

|  | Example 1 | Example 2 |
| --- | --- | --- |
| Mirror Type | Optical Component with multilayer coating of length 80 mm (for a source emitting the radiation CuKα and of size 50 microns) Ex: mirror FOX 3D 10_30 of XENOCS | Optical Component with multilayer coating of length 100 mm (for a source emitting the radiation CuKα and of size 50 microns) Ex: Mirror FOX 3D 14_39 of XENOCS |
| Distance source—centre of the mirror | 10 cm | 14 cm |
| Distance centre mirror—point of focussing | 30 cm | 39 cm |
| Distance outlet mirror—slit anti-diffusing | 13 cm | 13 cm |
| Distance outlet mirror—sample | 15 cm | 15 cm |
| Distance sample—detector | 15 cm | 24 cm |
| Qmin (theoretical) with a beamstop of 500 microns | 0.0095 Å$^{-1}$ | 0.0085 Å$^{-1}$ |
| Δq (Å$^{-1}$) (theoretical) | 0.003 Å$^{-1}$ | 0.005 Å$^{-1}$ | mator component relative to the direction of propagation of the X-rays ($P_{RX}$), said spatial delimitation anti-diffusing member comprising one or more plates having portions arranged to form a delimiting orifice, said portions being coated with a monocrystalline material limiting the scattering of X-rays;

a cut-off member of X-rays emitted by the source block, said cut-off member comprising X-ray absorption means arranged in the delivery device to cut off the direct X-ray beams emitted by the source block likely to reach the spatial delimitation anti-diffusing member without conditioning by the optical monochromator component;

wherein the cut-off member comprises an absorption blade formed from a material absorbing X-rays, said absorption blade being placed in the optical block opposite the optical monochromator component so as to cut off the X-rays likely to reach the spatial delimitation anti-diffusing member without conditioning by the optical monochromator component.

2. The device as claimed in claim 1, wherein the X-ray absorption means of the cut-off member are arranged to prevent the direct X-ray beams from going beyond the optical monochromator component in the direction of propagation of the X-rays ($P_{RX}$).

3. The device as claimed in claim 1, wherein the cut-off member comprises an absorption plate formed from a material absorbing X-rays and including a definition orifice, said absorption plate being arranged upstream of the optical monochromator component relative to the direction of propagation of the X-rays ($P_{RX}$), and said definition orifice having dimensions and a positioning provided to cut of the direct X-ray beams emitted by the source block likely to reach the spatial delimitation anti-diffusing member without conditioning by the optical monochromator component.

4. The device as claimed in claim 3, wherein the definition orifice of the cut-off member has reduced dimensions and a positioning provided to cut off part of the optical X-ray beams emitted by the source block directly impacting the reflecting surface of the optical monochromator component.

5. The device as claimed in claim 3, wherein the definition orifice of the cut-off member comprises inclined edges coated with a monocrystalline material provided to prevent the scattering of X-rays on said edges.

6. The device as claimed in claim 3, wherein the definition orifice and the delimiting orifice have the form of a slit.

7. The device as claimed in claim 3, wherein the definition orifice and the delimiting orifice have the form of a hole.

8. The device as claimed in claim 3, wherein the absorption plate of the cut-off member, the optical monochromator component and the spatial delimitation anti-diffusing member are fixed on the same monolithic support.

9. The device as claimed in claim 3, wherein the absorption plate of the cut-off member, the optical monochromator component and the spatial delimitation anti-diffusing member are arranged inside a casing adapted to be under vacuum, said casing comprising inlet and outlet walls formed from a material transparent to X-rays.

10. The device as claimed in claim 1, wherein the absorption blade comprises an inclined edge coated in a monocrystalline material provided to prevent the scattering of X-rays on said edge.

11. The device as claimed in claim 1, wherein the optical monochromator component is curved in a sagittal direction and in a meridional direction relative to the direction of propagation of the X-rays ($P_{RX}$), the absorption blade being arranged at the centre of the optical monochromator component so as to brush the reflecting surface.

12. The device as claimed in claim 1, wherein the absorption blade has a form complementary to the optical monochromator component.

13. The device as claimed in claim 1, wherein the spatial delimitation anti-diffusing member comprises a plate in which is formed the delimiting orifice, said delimiting orifice comprising inclined edges coated in the monocrystalline material provided to prevent the scattering of X-rays on said edges.

14. The device as claimed in claim 1, wherein the spatial delimitation anti-diffusing member comprises several plates, each plate having an inclined edge coated with the monocrystalline material provided to prevent the scattering of X-rays on said edge, said plates being arranged relative to each other such that said edges form the delimiting orifice in the direction of propagation of the X-rays.

15. The device as claimed in claim 1, wherein the distance between the outlet of the optical monochromator component and the inlet of the spatial delimitation anti-diffusing member is lower than 15 cm.

16. A device for delivery of a beam of X-rays for analysis of a sample, the sample being placed at the output of said delivery device, characterised in that the delivery device comprises:

a source block comprising X-rays emission means;

an optical block placed downstream of the source block relative to the direction of propagation of the X-rays ($P_{RX}$), said optical block comprising an optical monochromator component having a reflecting surface provided for conditioning X-rays emitted by the source block according to a unidimensional or bidimensional optical effect; and definition means of X-rays comprising:

an anti-diffusing member for spatially delimiting X-rays conditioned by the optical monochromator component, said spatial delimitation anti-diffusing member being arranged downstream of the optical monochromator component relative to the direction of propagation of the X-rays ($P_{RX}$), said spatial delimitation anti-diffusing member comprising one or more plates having portions arranged to form a delimiting orifice, said portions being coated with a monocrystalline material limiting the scattering of X-rays;

a cut-off member of X-rays emitted by the source block, said cut-off member comprising X-ray absorption means arranged in the delivery device to cut off the direct X-ray beams emitted by the source block likely to reach the spatial delimitation anti-diffusing member without conditioning by the optical monochromator component, wherein the cut-off member comprises an absorption blade formed from a material absorbing X-rays, said absorption blade being placed in the optical block opposite the optical monochromator component so as to cut off the X-rays likely to reach the spatial delimitation anti-diffusing member without conditioning by the optical monochromator component; and wherein the device further comprises a complementary cut-off member placed between the optical monochromator component and the spatial delimitation anti-diffusing member, said complementary cut-off member comprising an absorption plate of X-rays in which a complementary definition orifice is formed, the complementary definition orifice having dimensions and a positioning provided to cut off some of the X-rays conditioned by the optical monochromator component to then form the useful beam of X-rays for analysis of the sample.

17. The device as claimed in claim 1, wherein the reflecting surface of the optical monochromator component is formed by a multilayer coating, said optical monochromator component being also suitable for collimation of X-rays impacting said optical monochromator component in the direction of the sample.

18. An analysis system of a sample by X-rays comprising:
an X-ray delivery device for delivery of a beam of X-rays for analysis of a sample, the sample being placed at the output of said delivery device, characterised in that the delivery device comprises:
a source block comprising X-rays emission means;
an optical block placed downstream of the source block relative to the direction of propagation of the X-rays ($P_{RX}$), said optical block comprising an optical monochromator component having a reflecting surface provided for conditioning X-rays emitted by the source block according to a unidimensional or bidimensional optical effect; and
definition means of X-rays comprising:
an anti-diffusing member for spatially delimiting X-rays conditioned by the optical monochromator component, said spatial delimitation anti-diffusing member being arranged downstream of the optical monochromator component relative to the direction of propagation of the X-rays ($P_{RX}$), said spatial delimitation anti-diffusing member comprising one or more plates having portions arranged to form a delimiting orifice, said portions being coated with a monocrystalline material limiting the scattering of X-rays;
a cut-off member of X-rays emitted by the source block, said cut-off member comprising X-ray absorption means arranged in the delivery device to cut off the direct X-ray beams emitted by the source block likely to reach the spatial delimitation anti-diffusing member without conditioning by the optical monochromator component, wherein the cut-off member comprises an absorption blade formed from a material absorbing X-rays, said absorption blade being placed in the optical block opposite the optical monochromator component so as to cut off the X-rays likely to reach the spatial delimitation anti-diffusing member without conditioning by the optical monochromator component;
and an X-ray detector placed downstream of the sample relative to the direction of propagation of the X-rays ($P_{RX}$), and wherein the reflecting surface of the optical monochromator component is formed by a multilayer coating, said optical monochromator component being also suitable for focussing on the detector X-rays impacting said optical monochromator component.

19. The device as claimed in claim 7, wherein the hole is rectangular, square or circular.

\* \* \* \* \*